(12) United States Patent
Eberhard

(10) Patent No.: US 9,427,517 B2
(45) Date of Patent: Aug. 30, 2016

(54) PISTON PUMP AND DEVICE FOR FEEDING AND METERING A FLUID FOR MEDICAL PURPOSES BY MEANS OF A PISTON PUMP

(71) Applicant: B. BRAUN MELSUNGEN AG, Melsungen (DE)

(72) Inventor: Dietmar Eberhard, Kenzingen (DE)

(73) Assignee: B. BRAUN MELSUNGEN AG, Melsungen (DE)

( * ) Notice: Subject to any disclaimer, the term of this patent is extended or adjusted under 35 U.S.C. 154(b) by 0 days.

(21) Appl. No.: 14/384,176

(22) PCT Filed: Mar. 8, 2013

(86) PCT No.: PCT/EP2013/054770
§ 371 (c)(1),
(2) Date: Sep. 10, 2014

(87) PCT Pub. No.: WO2013/139630
PCT Pub. Date: Sep. 26, 2013

(65) Prior Publication Data
US 2015/0032054 A1  Jan. 29, 2015

(30) Foreign Application Priority Data
Mar. 19, 2012 (DE) .......................... 10 2012 102 272

(51) Int. Cl.
*A61M 1/00* (2006.01)
*A61M 5/142* (2006.01)
(Continued)

(52) U.S. Cl.
CPC ....... *A61M 5/14216* (2013.01); *A61M 5/1422* (2013.01); *F04B 7/0023* (2013.01); *F04B 7/0057* (2013.01); *F04B 13/00* (2013.01); *A61M 2205/3375* (2013.01)

(58) Field of Classification Search
CPC ............ A61M 5/142; A61M 5/1422; A61M 5/14216; A61M 5/1456; A61M 5/14566; A61M 5/14546; F04B 7/00; F04B 1/02; F04B 7/0023; F04B 7/0007; F04B 7/0038; F04B 7/0057; F04B 7/0061; F04B 39/10; F04B 39/1046; F04B 39/1066; F04B 39/14; F04B 53/109; F04B 53/22
USPC ....... 417/461, 415, 454, 510, 515, 516, 517, 417/518, 519, 521, 531, 532, 538, 539; 604/152
See application file for complete search history.

(56) References Cited

U.S. PATENT DOCUMENTS 3,802,265 A * 4/1974 Wood .................. G01P 5/14
                                                    73/715
4,854,836 A   8/1989 Borsanyi
(Continued)

FOREIGN PATENT DOCUMENTS

DE     38 38 689      6/1990
JP     48-644         10/1973
(Continued)

OTHER PUBLICATIONS

Chinese Office Action with translation for CN 201380015077.X dated May 5, 2015.
(Continued)

Primary Examiner — Theodore Stigell
Assistant Examiner — Tiffany Legette
(74) Attorney, Agent, or Firm — RatnerPrestia

(57) ABSTRACT

A piston pump is described for pumping a fluid, comprising at least two cylinders each having a piston which is movable inside the associated cylinder along the longitudinal axis of the cylinder by means of a drive, wherein cylinders are attached to a common pump flange. In each cylinder a chamber is formed having a volume that changes when the associated piston is moved in the cylinder. The pump flange extends along the direction of motion of the pistons, and at least one inlet port and one outlet port are attached to the pump flange, whose longitudinal axes run along the pump flange. A central valve plate is attached to the side of the pump flange facing away from the cylinders that bear on the pump flange and continuously rotates transversely to the pump flange during pumping operation of the piston pump. Respective passages are introduced to the pump flange in the region of each inlet and outlet port, and cylinder openings are introduced to the pump flange in the region of each cylinder. The valve plate has at least two cavities on the flange side, of which a first cavity coincides, upon rotation of the valve plate to a first angular position, with a cylinder opening of a first cylinder and a passage of the outlet port, while the second cavity coincides in this first angular position with the passage of the inlet port and a cylinder opening in the second cylinder. The first cavity then coincides, upon rotation of the valve plate to a second angular position, with the passage in the outlet port and a cylinder opening in the second cylinder, while the second cavity coincides in this second angular position with the passage in the inlet port and a cylinder opening in the first cylinder.

15 Claims, 10 Drawing Sheets

(51) Int. Cl.
*F04B 7/00* (2006.01)
*F04B 13/00* (2006.01)

(56) References Cited

U.S. PATENT DOCUMENTS

| | | | |
|---|---|---|---|
| 5,312,233 | A | 5/1994 | Tanny et al. |
| 7,887,308 | B2 | 2/2011 | Navarro |
| 2004/0204679 | A1* | 10/2004 | Visconti ............ A61B 17/00234 604/131 |
| 2008/0294040 | A1* | 11/2008 | Mohiuddin ....... A61M 5/14216 600/432 |
| 2011/0021990 | A1 | 1/2011 | Navarro et al. |
| 2011/0206545 | A1 | 8/2011 | Junod et al. |

FOREIGN PATENT DOCUMENTS

| | | |
|---|---|---|
| JP | 1996-219008 | 8/1996 |
| JP | 2000-356183 | 12/2000 |
| WO | WO 2008/086349 | 7/2008 |

OTHER PUBLICATIONS

International Search Report for PCT/EP2013/054770 dated May 17, 2013.
German Search Report and Written Opinion for DE 10 2012 102 272.0 dated Jun. 10, 2014.
Japanese Office Action (with translation) for JP 2015-500835 dated Feb. 2, 2016.

* cited by examiner

Position 0°

Position 30°

Position 180°

Position 210°

PISTON PUMP AND DEVICE FOR FEEDING AND METERING A FLUID FOR MEDICAL PURPOSES BY MEANS OF A PISTON PUMP

CROSS REFERENCE TO RELATED APPLICATIONS

This application is the U.S. national phase application of PCT International Application No. PCT/EP2013/054770 filed Mar. 8, 2013, which claims priority to German Patent Application No. DE 10 2012 102 272.0 filed Mar. 19, 2012, the contents of each application being incorporated by reference herein.

FIELD OF THE INVENTION

The invention relates to a piston pump for pumping a fluid, comprising at least two cylinders each having a piston which is movable inside the associated cylinder along the longitudinal axis of the cylinder by means of a drive, wherein the cylinders are attached on a common pump flange. In each cylinder a chamber is formed having a volume that changes when the associated piston is moved in the cylinder.

Furthermore the invention relates to an apparatus for supplying and metering a fluid for medical purposes, wherein the apparatus includes such a piston pump.

BACKGROUND

Piston pumps are particularly suited for use in medical infusion technology. Predominantly tube pumps and injection pumps are currently in use. Tube pumps which work according to the peristaltic principle are used above all when larger quantities of fluid are to be administered. A provision of these quantities of fluid occurs for example by means of an infusion bag. In the case of syringe pumps the delivery volume through the injection body is limited and includes generally not more than 50 ml, wherein some models even allow a liquid supply of up to 100 ml.

Tube pumps according to the peristaltic principle are very widespread and are also ambulatory, e.g., used for artificial nutrition. Because of its pump principle, their delivery accuracy is, however, worse than that of injection pumps. Furthermore the secure closing of the inlet and outlet ports is crucial, wherein conventional infusion sets, whose fluid delivery function is facilitated via a peristaltic segment, usually comprise a so-called "free flow clamp" to eliminate a gravity-induced fluid flow which simply squeezes the tube.

DESCRIPTION OF THE RELATED ART

In these areas of application a reliable occlusion detection is in addition indispensable because an unrecognized under-delivery may carry a high medical risk. The detection of an occlusion takes place usually by an indirect measurement of the internal pressure in a tube which serves for supplying a fluid to a patient. If an occlusion exists, the internal pressure of the tube downstream from the pump for example increases, which can be indirectly measured. For this purpose, the tube's round cross-section is often deformed elliptically by a biasing force and the tube's internal pressure to be determined increases or reduces this biasing force which then may be determined by means of a force sensor. DE 38 38 689 C1 discloses exemplarily such a method for pressure measurement and occlusion detection.

When inserting a tube set in a pump, according to the current state of the art, the tube segment responsible for an occlusion sensor must additionally be inserted by hand into special supports, which can be problematic not only in the field of home care. Furthermore this method has the disadvantage that the deformation of the tube leads generally to a creep process lasting hours. This creep releases tension in the tube cross-section which leads to a continuous changing of the measured force. The undesired change in force caused by the creeping is of a similar order of magnitude to the desired measuring effect by means of variation of the tube inner pressure and therefore hinders the reliable recognition of an occlusion. Special elastomers such as for example silicone comprise a significantly reduced creep behavior and are therefore predestined as the tube segment for the occlusion sensor. A combination of silicon with non-silicone materials is however very costly because process-safe bonded joints are not possible.

Periodically operating piston pumps comprise a high delivery accuracy as with syringe pumps, and can suck in and pump out liquids from an exchangeable storage tank as with peristaltic pumps. Such a pump is for example described in U.S. Pat. No. 7,887,308 B2. This document discloses various piston pumps having a valve plate that rotates back and forth in order to ensure the pumping function. However its function is limited to a single pumping function. Since the inlet and outlet connections are attached to the reciprocating valve plate, the connecting tubes furthermore move with the pump motion, whereby much space is required.

Furthermore, in the case of the pumps known from U.S. Pat. No. 7,887,308 B2, a necessary occlusion sensor cannot be integrated compactly into the pump body. Due to three mechanical couplings for the drive (2×pistons and 1×valve plate), the drive interface of the pump according to U.S. Pat. No. 7,887,308 B2 furthermore is mechanically highly overdetermined, whereby the loading is made difficult. Complex and precise guides of the pump during insertion or removal are compulsory for a safe and simple handling.

A free-flow clamping function or further sensor components are also not integrated for the pump embodiments of U.S. Pat. No. 7,887,308 B2. In the case of an infusion set that is not inserted into the pump body, a pumping can take place by a filling of the cylinder by means of a pressure-induced movement of the pistons. In contrast to the usual filling before therapy (priming) of an infusion set by means of gravity, the piston pump described in U.S. Pat. No. 7,887,308 B2 allows only a filling of the infusion set through commissioning of the piston pump itself. If for example infusion sets are filled in a central clinical unit and are to be subsequently loaded into other pump drives in the vicinity of the patient, the filling must be completed with a defined piston and valve plate setup, since otherwise loading into the other pump drive is not possible. Since the end of a filling hardly corresponds at all with this initial position of piston and valve plate, an over-delivery is necessary, which leads to a leakage of fluids at the patient end of the infusion set.

Relevant state of the art is also known from documents US 2011/0021990 A1, US 2011/0206545 1 and U.S. Pat. No. 4,854,836 A.

SUMMARY OF THE INVENTION

An object of aspects of the invention is therefore to provide a piston pump and with it also an apparatus for supplying and metering a fluid for medical purposes, which apparatus enables a compact construction and easy handling both for the pumping function and for additional components such as an occlusion sensor and ultrasound sensor. Furthermore a reliable locking function should be realizable.

The piston pump according to aspects of the invention serves to pump a fluid and comprises at least two cylinders each having a piston which is movable inside the associated cylinder along the longitudinal axis of the cylinder by means of a drive. Thereby the cylinders are attached to a common pump flange, and a chamber is formed in each cylinder, having a volume that changes when the associated piston is moved in the cylinder.

According to aspects of the invention the pump flange extends along the direction of motion of the pistons, and at least one inlet port and one outlet port are attached to the pump flange, whose longitudinal axes also run along the pump flange. In a preferred exemplary embodiment of the invention the pump flange extends parallel to the direction of motion of the pistons, and the inlet and outlet ports also run parallel to the pump flange. However deviations from parallelism are also covered by the invention such that also the pump flange may extend only in the direction of motion of the piston, while the inlet and outlet ports also run in the direction of the pump flange. The deviation from parallelism may for example be in the order of 1-20°, but is not limited to these values.

Furthermore according to aspects of the invention, a central valve plate is attached to the side of the pump flange facing away from the cylinders, which valve plate bears on the pump flange and continuously rotates during pumping operation of the piston pump. Thereby the axis of rotation of the valve plate runs transversely and preferably perpendicularly to the pump flange. Respective passages in the region of the inlet and outlet port, and respective cylinder openings in the region of the cylinders are introduced into the pump flange, wherein the valve plate on the flange side comprises at least two cavities of which a first cavity coincides, upon rotation of the valve plate to a first angular position, with a cylinder opening of a first cylinder and a passage of the outlet port, while the second cavity coincides in this first angular position with the passage of the inlet port and a cylinder opening in the second cylinder. Furthermore the first cavity coincides, upon rotation of the valve plate to a second angular position, with the passage in the outlet port and a cylinder opening in the second cylinder, while the second cavity coincides in this second angular position with the passage in the inlet port and a cylinder opening in the first cylinder.

By means of this arrangement of cylinders, ports and a valve plate at a common flange, the piston pump according to aspects of the invention can have a very compact construction, without stationary or mobile parts requiring too much space. This is particularly true when the longitudinal axes of the cylinders and/or the longitudinal axes of the inlet and outlet ports run approximately in the same direction or even parallel to each other. Furthermore the directions of movement of the pistons are preferably the same.

In contrast to the pump known from U.S. Pat. No. 7,887,308 B2, for example, the plane of the valve plate is furthermore essentially parallel to the main assembly plane of the pump. Since the valve plate must be mechanically coupled to the drive upon insertion, improved mechanical design possibilities arise which involve an improved ergonomic handling. For example a complex double-eccentric drive is not required for the functional control of the pump, such as provided in U.S. Pat. No. 7,887,308 B2. Also moving tube segments can be avoided, which permits a clearly simpler assembly.

In addition a clearly higher accuracy is achieved by the piston pumping principle in comparison to peristaltic pumps. In particular in the case of the short-term flow constant, which is apparent from the so-called "trumpet curve", the piston pumping principle is clearly superior to the peristaltic pumping principle. The tolerance requirements are also clearly reduced through a valve plate, which has a sealing function only on one side.

In one exemplary embodiment of the invention, upon rotation of the valve plate to at least a third position, the cavities of the valve plate do not coincide with a cylinder opening. Before removal of the infusion set, the valve plate may therefore be rotated by a suitable motor-driven turning to a position in which a complete free-flow protection is possible, analogous to peristaltic infusion sets. Preferably this at least a third angular position lies between the two previously stated angular positions in which the two cylinders suck or eject.

Preferably the drive brings about the movement of the pistons as well as the rotation of the valve plate. Thereby the drive in one exemplary embodiment of the invention is an eccentric drive having an eccentric disc and a frame surrounding the eccentric disc, wherein the rotation point V of the valve plate deviates from the rotation point E of the eccentric disc. Furthermore a rotational drive unit brings about the rotation of the valve plate during pumping operation of the piston pump, wherein the drive unit is coupled to the eccentric disc such that the eccentric disc rotates with the valve plate and makes contact on the frame at two opposite-lying frame flanks, whereby the frame reciprocates in the direction of the two frame flanks. The pistons are each coupled to the frame such that the reciprocating motion of the frame can be transferred to the pistons. In this way both the movement of the pistons and also the rotation of the valve plate may be realized in a compact fashion through a common drive.

Preferably the eccentric disc is thereby releasably coupled to the drive unit. For this purpose the eccentric disc may for example be configured as a ring and surround the drive unit, wherein the drive unit comprises a nose at its outer periphery while the eccentric disc comprises a pin at its inner periphery, which pin bears on the nose during pumping operation of the piston pump. If the valve plate then is rotated backwards by the drive unit, the nose releases itself from the pin and the current position of the pistons and the valve plate can be fixed. In this way the type of the drive may be advantageously used for a free-flow clamping function.

Optionally at least one occlusion sensor may be integrated into the inlet port, the outlet port and/or the pump flange respectively, which occlusion sensor cannot be non-destructively disassembled, wherein the inlet port, the outlet port and/or the pump flange may serve as a housing of the occlusion sensor.

For example, in addition at least one recess may be provided in a thus formed housing, which recess is tightly covered by a sensor component composed of a pressure sensitive material. Thereby the material of the housing is harder than that of the sensor component, and the piston pump comprises a force sensor with which pressure-induced changes of the sensor component in the region of the respective recess can be measured.

The invention thus makes use of the operating principle of a pressure membrane, but does not use this in a separate element, rather it integrates a corresponding sensor component into the housing composed of a hard material, through which a fluid is delivered anyway. Thereby the occlusion sensor's mechanical sensor component to be integrated rests on the principle of the measurement of pressure in the fluid and is realized by means of an elastic material which behaves physically analogously to a pressure membrane. A port and/or the pump flange itself form/s thereby a hard component insensitive to pressure which does not deform during the pressure changes that occur. Due to the occurring deformations of the sensor component as soft component on the other hand, the internal pressure in the port can be deduced.

The occlusion sensor may be integrated directly into such a housing so as to save space, which permits a very compact design. A port may be an inlet and/or outlet port which conducts the fluid to a pump or from the same to a patient. In this way the sensor can recognize occlusions ahead of and/or behind a pump. If the associated port is suitably positioned such that it can be compactly accommodated with a pump in a housing, then the occlusion sensor at this port does not require much more space.

The sensor component is thereby preferably an integral and non-removable component of a respective housing, such that it also does not have to be installed or even aligned in the event of commissioning of the apparatus. This facilitates the handling of the apparatus and avoids setup errors and thus also measurement errors.

Preferably the force sensor is in contact in the region of a recess in the housing with the surface of the sensor component, wherein the force sensor comprises for example a plunger which is in direct contact in the region of the recess with the surface of the sensor component. In this way a change in the expansion of the sensor component in this region can be measured.

Furthermore, for this purpose, the sensor component is composed of an elastomer wherein in particular it can be a silicon or a thermoelastic elastomer. In this way the physical properties of this special elastomer can be advantageously used, which in particular comprises a low creep behavior. A material-fit connection of silicone and non-silicone materials is however not required since appropriate methods, such as for example injection molding methods, can be used for a sealed connection between port and sensor component. In this way the respective housing and the sensor component may be manufactured in a two-component process. Alternatively the connection between port and sensor component may be manufactured by means of other connection techniques wherein for example plug-in, click, screw or adhesive joints are possible.

In one exemplary embodiment of the occlusion sensor the sensor component is a tube which surrounds a port with form-locking fit such that it tightly covers a recess in the port from the outside. In another exemplary embodiment said tube is attached with form-locking fit inside a port such that the sensor component tightly covers a corresponding recess in the port from inside. The port and the sensor component have for this purpose a similar or the same cross-section. For example a tube having a round cross-section may be introduced with form-locking fit into a round port, or may enclose the same.

Also, however, it can be advantageous when the sensor component has an elliptical cross-section, wherein a flat side of the sensor component is arranged in the region of the recess. This may be the case for inner as well as for outer lying sensor components, wherein the cross-section of the port may be correspondingly adjusted. By means of this form of soft component, the sensor component already has the elliptical deformation necessary for the internal pressure measurement, such that undesired creep behaviors with thermoplastic elastomers can be prevented already to the greatest possible extent.

The elliptical cross-section may for example be achieved by means wherein a tube having originally circular cross-section is suitably deformed before it is assembled to an inlet or outlet port. The deformation is then not brought about through the assembly, but rather there occurs a pre-deformation of the tube to the desired elliptical cross-section in order to prevent undesired creep behavior.

In another exemplary embodiment of the occlusion sensor, the sensor component is a specially shaped measurement membrane having a cross-section comprising at least two opposite-lying membrane sides which each are kinked inwards, while a membrane top side which connects the two membrane sides to each other is formed straight and is arranged in the region of the recess. The force sensor thus lies on a straight surface of the measurement membrane, which is no longer changed by internal stress, such that a linear force characteristic results.

Further optionally, an ultrasound sensor may be integrated into an inlet port and/or outlet port respectively, for the detection of air bubbles in the respective port, which ultrasound sensor preferably also cannot be non-destructively disassembled. In one exemplary embodiment of the invention, the ultrasound sensor is executed such that a tube is inserted with form-locking fit into the inlet and/or outlet port, through which fluid is supplied to the inlet port or discharged from the outlet port. Thereby surfaces for the coupling and decoupling of ultrasound are provided in the region of the tube at two sides of the relevant inlet and/or outlet port. These surfaces for the coupling and decoupling of ultrasound may be executed flat, however they can also comprise differently formed surfaces suited to the form of the ultrasonic sensors.

The inlet and/or outlet port is preferably formed such that these surfaces lie in a plane. Furthermore it may be practical for the inlet and/or outlet port to comprise a recess in order to prevent a possible short circuit path of the ultrasound path past the tube piece to be examined. In one exemplary embodiment of the invention this recess lies opposite to the surfaces for the coupling and decoupling of ultrasound, however the recess may be arbitrarily arranged. Also a plurality of recesses are possible for this purpose.

Possible areas of application of a thus formed pump are (not exclusively): medical single-use articles of infusion or dialysis systems, or devices having single-use articles for the individual dosage of drugs such as in the pharmacy field. The safe closing of the inlet and outlet ports is crucial here. The described arrangement may be integrated into a medical infusion set and can replace the peristaltic segment necessary for the delivery. However the invention is not limited to the application in infusion sets, rather it comprises general apparatuses for supplying and metering a fluid for medical purposes, wherein the respective apparatus comprises the piston pump according to aspects of the invention.

Mechanical apparatuses may then be integrated into the piston pump in addition to the pure pumping function, wherein said mechanical apparatuses form the mechanical part of the required fluid sensors and constitute a simple mechanical interface to the external electronic sensor components. Thus by the implementation with a sensor component in a port, the pressure measuring segment which is important for the occlusion sensor can also be replaced. By means of the optional interface to an ultrasound sensor which can recognize potential air bubbles, another prerequisite for a compact cassette system for the pump-and-sensor unit is achieved.

The mechanical sensor components thereby do not have to be deployed as independent components in the pump module through costly mounting or assembly techniques, rather they can form integral and non-removable components of the pump. To this end, intelligent arrangements and a mechanical design have been found, which take into account economical manufacturing techniques and in particular multi-component injection molding techniques. The pump itself may be realized as a periodically operating piston pump, in order to join the advantages of the high delivery accuracy and the ability to deliver from one supply bag.

The described arrangement is however not limited to the pumping of fluids. With good sealing of the valve plate, even the pumping of gases by the piston pumping principle is not excluded.

BRIEF DESCRIPTION OF THE DRAWINGS

The invention is best understood from the following detailed description when read in connection with the accompanying drawings. Included in the drawings are the following figures:

FIG. 6b shows a cross-section through a pump flange according to FIG. 6a;

DETAILED DESCRIPTION OF THE PREFERRED EMBODIMENTS

Figure 1A:
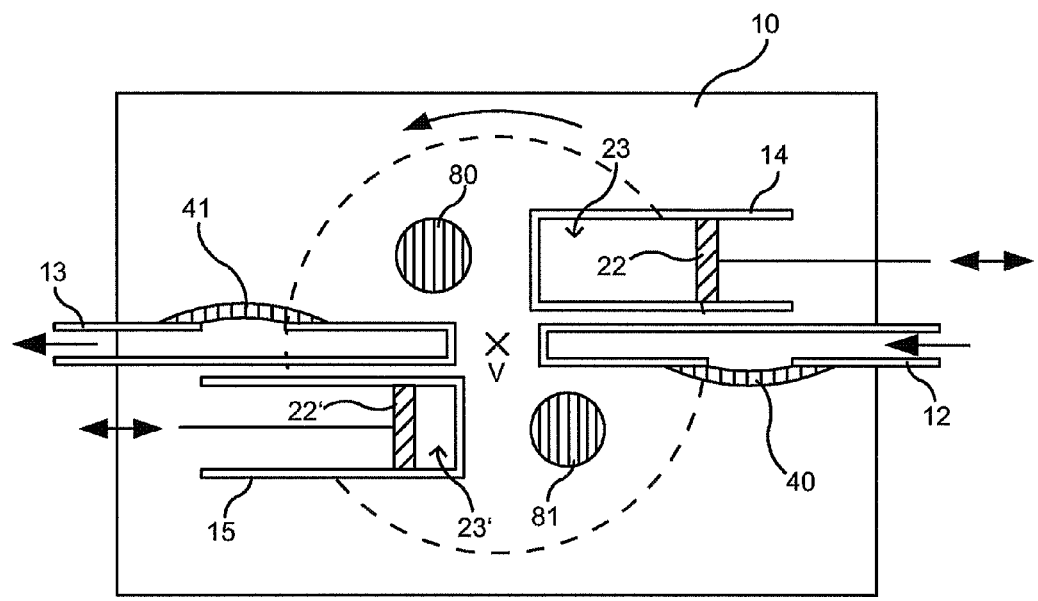
FIG. 1a shows a schematic representation of the functional principle of an exemplary embodiment of a piston pump in a plan view.
Figure 1B:
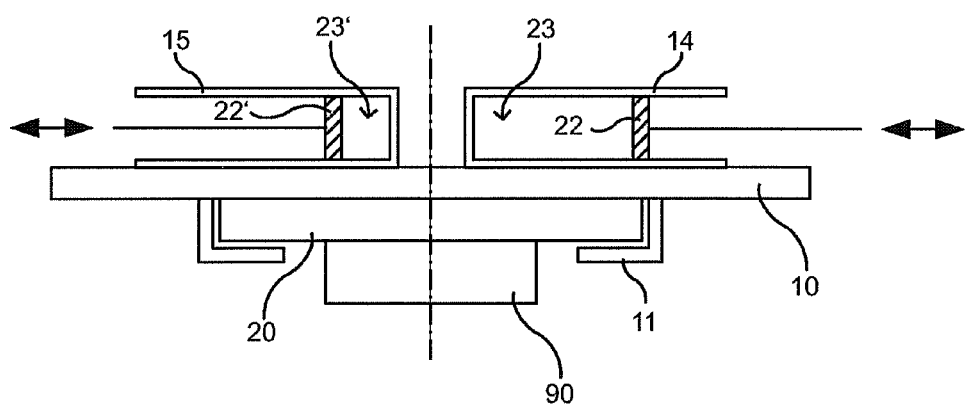
FIG. 1b shows a piston pump according to FIG. 1 in a schematic cross-section.

FIG. 1a shows a schematic representation of an exemplary embodiment of a piston pump in a view which is complemented by a corresponding cross-section in FIG. 1b. Thereby one or a plurality of cylinders 14, 15 each having reciprocatingly movable pistons 22, 22' are fixed to a planar pump flange 10. The pistons 22, 22' are located within respective chambers 23, 23' of respective cylinders 14, 15. Further components fixed to the flange 10 include an inlet port 12 and an outlet port 13. The fluid to be delivered then flows for example from a storage tank and tube system into the inlet port 12, while it flows out from the outlet port 13 and is delivered to a patient via a further tube system.

Furthermore at least one sensor 40, 41, 80, 81 is provided on the pump flange 10 which can also be described as a mounting flange, which sensor serves to recognize an occlusion. The sensor for the occlusion detection may be integrated either on the flange 10 itself and/or into the delivering or discharging pump ports 12, 13. The sensors which are connected on the flange 10 with supply or outlet channels are indicated in the exemplary embodiment of FIG. 1a with 80 and 81, whereas the sensors integrated directly into the inlet or outlet ports 12, 13 are indicated with 40 and 41.

The valve function is realized through a centrally arranged rotating valve plate 20 which is located below the flange 10 and may be mounted for example via a flange bracket 11 at the flange 10. This valve plate 20 is connected via openings in the flange 10 with the cylinders 14, 15 or the pump ports 12, 13. The valve plate 20, in the pumping operation of the pump, continuously rotates about its rotation point in one direction, which is shown in FIG. 1a by a curved arrow, wherein the drive below the valve plate 20 in FIG. 1b is indicated schematically by the reference sign 90.

This type of pump is characterized in that the piston movement is mechanically derived from the rotary motion. Within a certain angular time period the pistons 22, 22' are however stationary in order to allow a valve switchover that is free of pressure shocks. During this changeover the piston function changes from the suction operation to the pumping operation. A change in the direction of rotation of the valve plate 20 can also lead to a change of the piston function. On the other side, the backward rotation may also be used for other mechanical purposes.

The interaction between valve plate position and piston function is shown in FIGS. 2 and 3a to 3c. The connection between valve plate 20 and cylinders 14, 15 occurs via several openings which are shown exemplarily by the openings 32, 33 and 34, 35 and form an entry and an exit in each cylinder. In each port 12, 13 there are also provided respective passages 30 and 31 which connect the ports to the valve plate 20, and also to the cylinders 14, 15 with a suitable position of the valve plate 20.

The pistons 22, 22' are in connection with the drive 90 via an external attachment point 26, 27 and are thus moved horizontally alternately to the left and right. In the case that several pistons 22, 22' are used, the direction of motion of both pistons 22, 22' is preferably the same.

Figure 2:
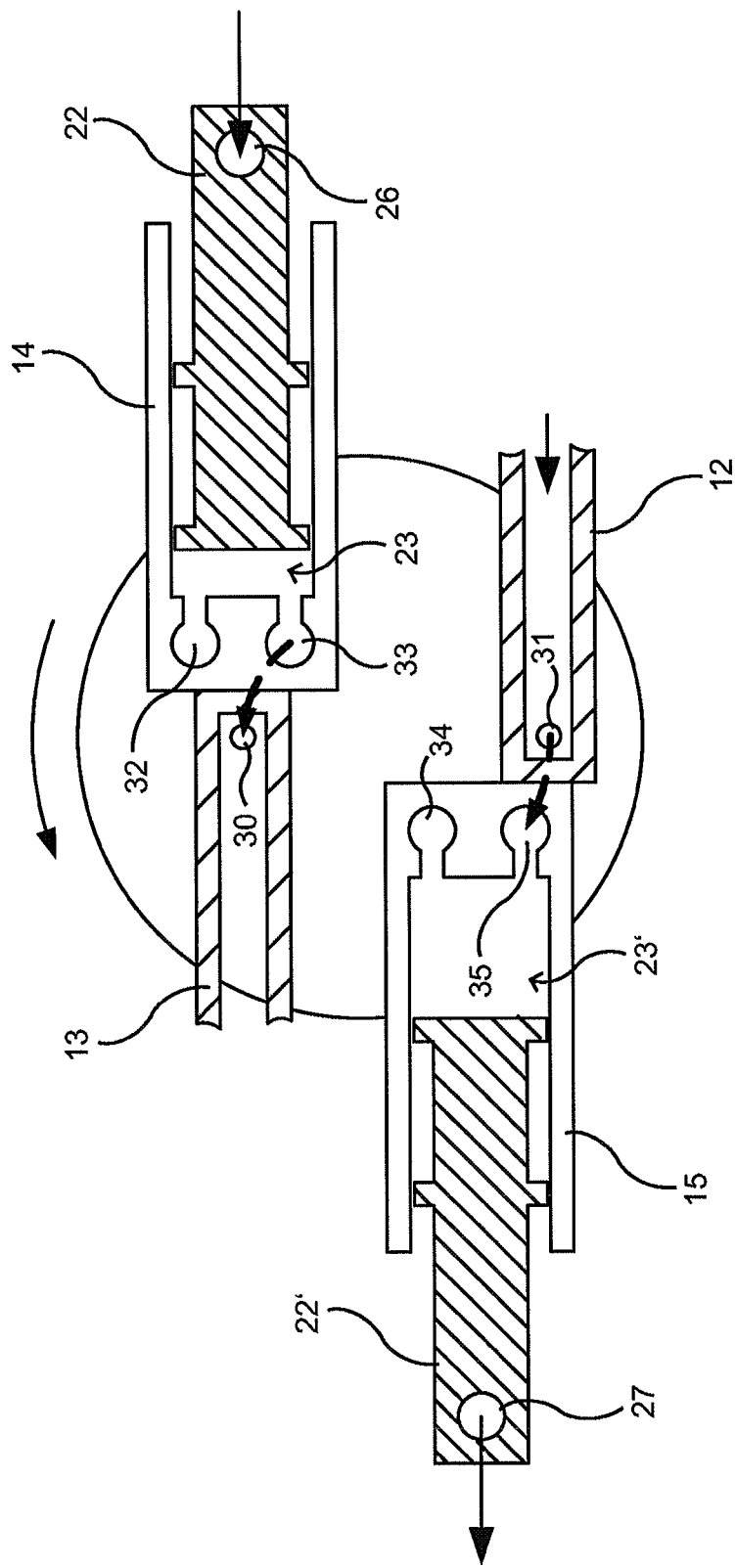
FIG. 2 shows a schematic representation of the piston pump with rotating valve plate.

In the case of the piston movement shown in FIG. 2, the cylinder 15 sucks fluid from the inlet port 12 via the inlet opening 35. The fluid passes from the inlet port 12 via the connection opening 31 to the valve plate 20 and subsequently reaches the cylinder 15 via the inlet opening 35.

Inside the valve plate 20, cavities on the flange side are suitably executed such that they can create or prevent this connection, wherein this route is shown with a broken arrow in FIG. 2.

In the same time period cylinder 14 pumps fluid in the direction of the outlet port 13. Thereby the fluid takes the path from the cylinder 14 via the outlet opening 33 in the valve plate 20. Inside this it passes via a channel inside the valve plate 20 through the connection opening 30 into the outlet port 13. This route is also shown in FIG. 2 with a broken arrow. After half of one rotation of the valve plate 20, cylinder 15 takes over the pumping of the fluid sucked up in the previous time period, via the outlet opening 34 and the opening 30 into the outlet port 13. In the same time period cylinder 14 sucks in fluid via its inlet opening 32 from the inlet port 12. For this purpose the valve plate 20 must be suitably executed in order to establish different routes between ports and cylinders in various valve plate positions.

The principal function of the valve plate 20 is thereby realized for example through recessed channels 24 and 25, which are configured on the flange side of the valve plate 20 (FIGS. 3a to 3d). The cavities 24, 25 may thereby be formed through circular, curved or straight recessed channels. The sealing function between valve plate 20 and flange 10 may be realized differently, wherein in addition to fluid, also gases could be pumped, with suitable sealing. By rotating the valve plate 20, the channels 24, 25 then pass under the cylinder entry or exit openings 32, 33, 34 and 35, and create a connection to the passages 30, 31 of the inlet port 12 or of the outlet port 13.

Figure 3A:
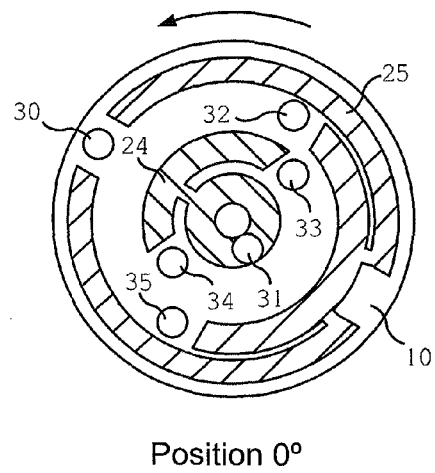
FIG. 3a shows the interaction between piston position and valve plate position at 0°.

If the valve plate 20 is located as in FIG. 3a in its initial position of 0°, then the channel 25 is connected neither with an opening 30, 31 in a port 12, 13, nor with the openings 32, 33, 34, 35 to the cylinders 14, 15, whereby the fluid flow through the outlet port 13 is completely prevented. Although the second channel 24 is indeed connected via the opening 31 to the inlet port 12, a connection to the cylinder openings 32, 33, 34, 35 is however not present. Thus also the entry of fluid through the inlet port 12 is completely prevented.

Figure 3B:
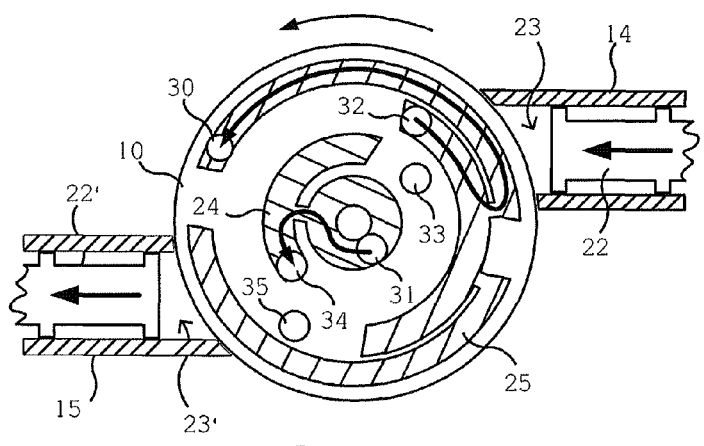
FIG. 3b shows the interaction between piston position and valve plate position at 30°.

From a certain angular position of the valve plate 20, which is provided through geometric boundary conditions, the fluid inlet 12 is opened toward the then sucking piston 22'. The same applies to the fluid outlet 13 which is connected to the ejecting piston 22. This is shown in FIG. 3b for an angular position of 30°. In a real implementation this angular position may however be distinctly smaller, and the relatively large value of 30° has been selected here to only give a clear illustration. In detail, the entry fluid path passes in this position from the inlet port 12 via the opening 31 to the channel 24 of the valve plate 20. This channel 24 is connected to the sucking piston 22' via the opening 34. The ejecting piston 22 pumps the fluid via its opening 32 into the channel 25 and from there via the opening 30 into the outlet port 13.

Figure 3C:
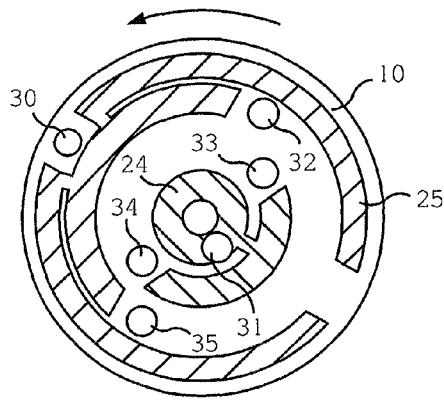
FIG. 3c shows the interaction between piston position and valve plate position at 180°.

This pumping direction is interrupted again at a further determined angular position, and the outlet opening 30 into the outlet port 13 is separated again from the channel 25, as shown for the angular position 180° in FIG. 3c. Channel 24 is also separated from the cylinder openings 32, 33, 34, 35 and the same sealing situation arises as in the angular position 0°.

Figure 3D:
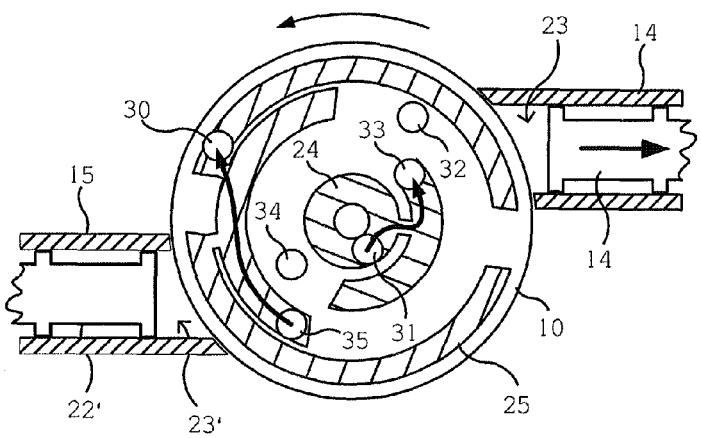
FIG. 3d shows the interaction between piston position and valve plate position at 210°.

A further rotation of the valve plate leads to a situation as shown for an angular position of 210° in FIG. 3d. Cylinder 15 is now connected via the cylinder opening 35 to the channel 25 and from there via the opening 30 to the outlet port 13 such that cylinder 15 is changed from the sucking cylinder to the ejecting cylinder. Cylinder 14 by contrast changes its function from ejecting cylinder to sucking cylinder via a fluid path which leads from the inlet port 12 via the passage 31 and the opening 33 to the cylinder 14.

A further rotation of the valve plate 20 blocks again the inlet port 12 and the outlet port 13 starting from a determined position, as was already shown exemplarily for the angular position of 0° in FIG. 3a.

The piston drive concept derived from the valve plate drive may be realized via different mechanical concepts. In addition the drive concept must ensure, in addition to the actual piston movement, a secure stationary position of the pistons 22, 22' within a determined angular range of the valve plate 20, which position serves the functional swapping of the cylinders 14, 15 from the suction to the pumping operation and vice versa. For example this may be achieved through an eccentric drive 90, as is shown schematically in FIGS. 4 and 5.

A rotational drive unit 92 is located below the valve plate 20 in the case of this eccentric drive 90, which rotational drive unit 92 is directly coupled with the valve plate 20 and rotates the same about its central rotation point V. The rotational drive 92 is surrounded by a ring-shaped eccentric disc 91 having a rotation point E which deviates from the rotation point V of the valve plate 20. It is decisive for the realization of a free-flow clamping function that the eccentric disc 91 is not rigidly coupled to the rotational drive 92. The linking of the rotary motion is rather accomplished via a nose 93 which is fixed to the outer periphery of the rotational drive 92. The linking of the two rotations occurs in the forward direction of rotation via a pin 94 which is attached to the inner periphery of the eccentric disc 91. If the drive 92 and with it the valve plate 20 rotates, as is shown in FIG. 4 for a forward direction of rotation with curved arrows, the eccentric disc 91 is carried away via the nose 93 which bears on the pin 94.

The eccentric disc 91 is surrounded by a horizontally displaceable frame 100, wherein the frame 100, during rotation of the eccentric disc 91, makes contact at the frame's flanks 101, 102. The frame 100 is connected via the bearing 103 to two horizontal guide rods 110, 120 such that the rotation of the eccentric disc 91 leads to a horizontal reciprocating motion of the frame 100. Shown in FIG. 4 is the right turning point of the frame 100. Contact with the pistons 22, 22' is then made via the attachment points 26, 27, wherein piston 22 in the shown frame position is maximally extended, since it is connected to the attachment point 26. Piston 22' is connected to the attachment point 27 and completely inserted.

Figure 4:
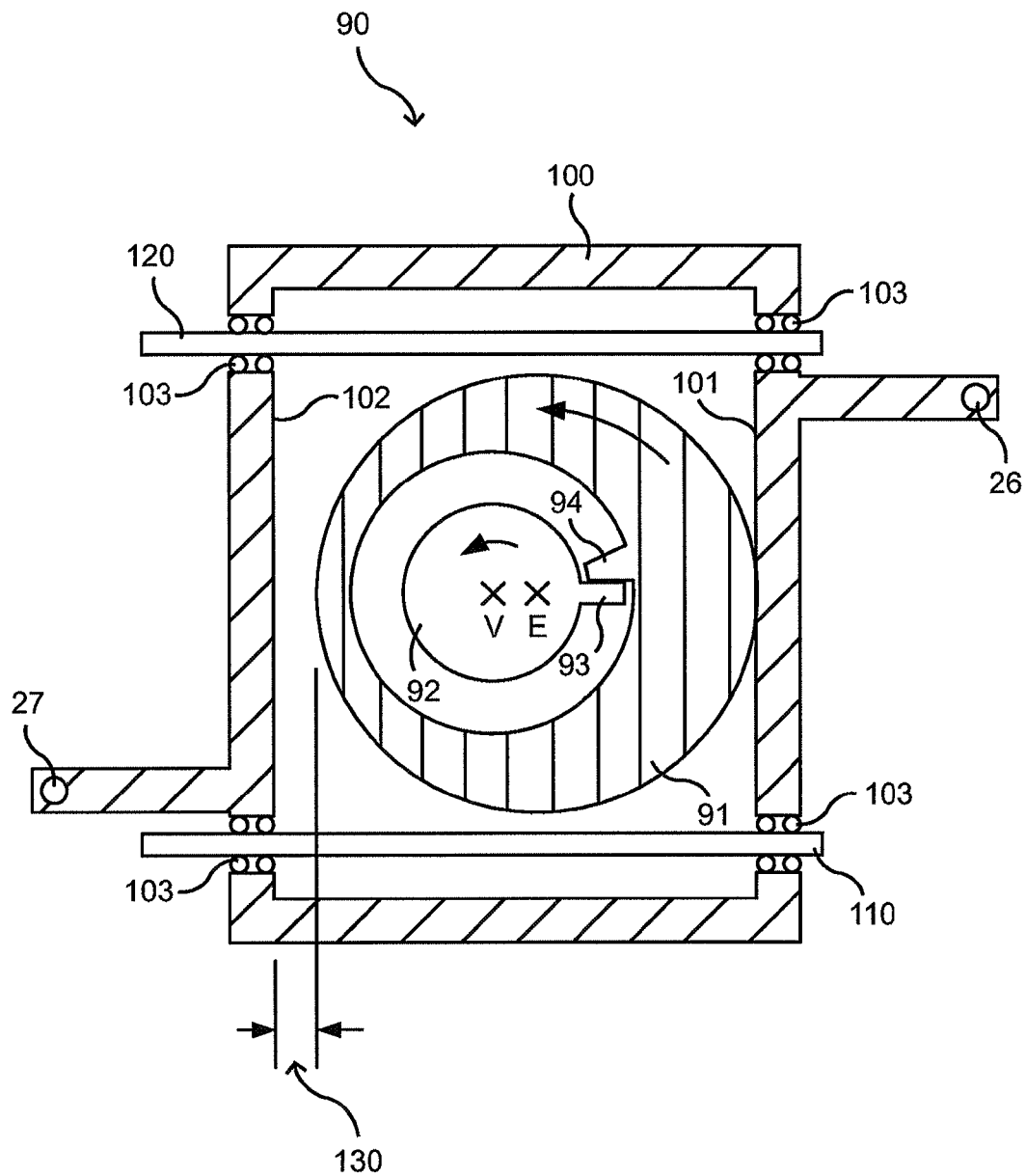
FIG. 4 shows a schematic representation of an exemplary embodiment of an eccentric drive for a piston pump according to aspects of the invention.

From FIG. 4 it is further evident that the distance between the two frame flanks 101 and 102 is bigger than the diameter of the eccentric disc 91. This difference is given by the gap dimension 130. During the time that the eccentric disc 91 requires in order to run from the frame edge 101 to the opposite-lying frame edge 102, the pistons are at rest. The valve function of the valve plate 20 must have completely switched within this angular range. The size of the gap dimension 130 must therefore be exactly matched to the valve plate geometry.

Figure 5:
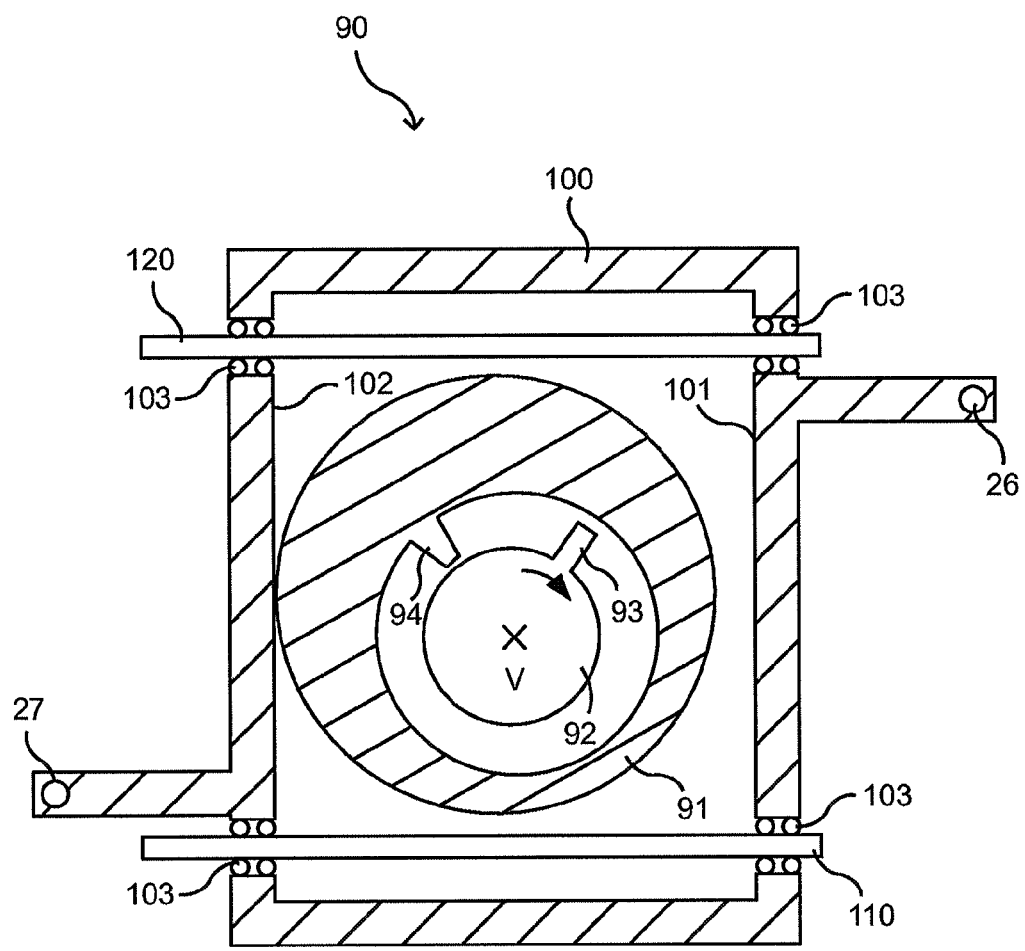
FIG. 5 shows the closing of the valve by means of an eccentric drive according to FIG. 4.

If after switching off the pumping function an additional blocking of the inlet and outlet ports 12, 13 is required, this is possible through a backward movement of the valve plate 20. This situation is shown in FIG. 5. By means of a backward movement of the rotary drive unit 92, the nose 93 releases itself from the pin 94 of the eccentric disc 91. The eccentric disc 91, the frame 100 and thereby the pistons 22, 22' remain in their current position. By means of the rigid coupling between the rotational drive 92 and the valve plate 20, it is possible to reach the valve plate positions indicated with 0° or 180° in FIGS. 3a and 3c, which brings about a complete closing of the ports 12, 13.

An optional occlusion sensor integrable into the pump according to aspects of the invention is preferably based on the principle of the pressure measurement in the fluid and uses as a mechanical sensor interface a membrane composed of a flexible material. This membrane may be made in a two-component process by injection molding, wherein the hard component is used for the housing and the soft component for realizing the actual measurement membrane. Thereby a housing as hard component may be realized optionally by the pump flange and/or one inlet and outlet port.

Figure 6A:
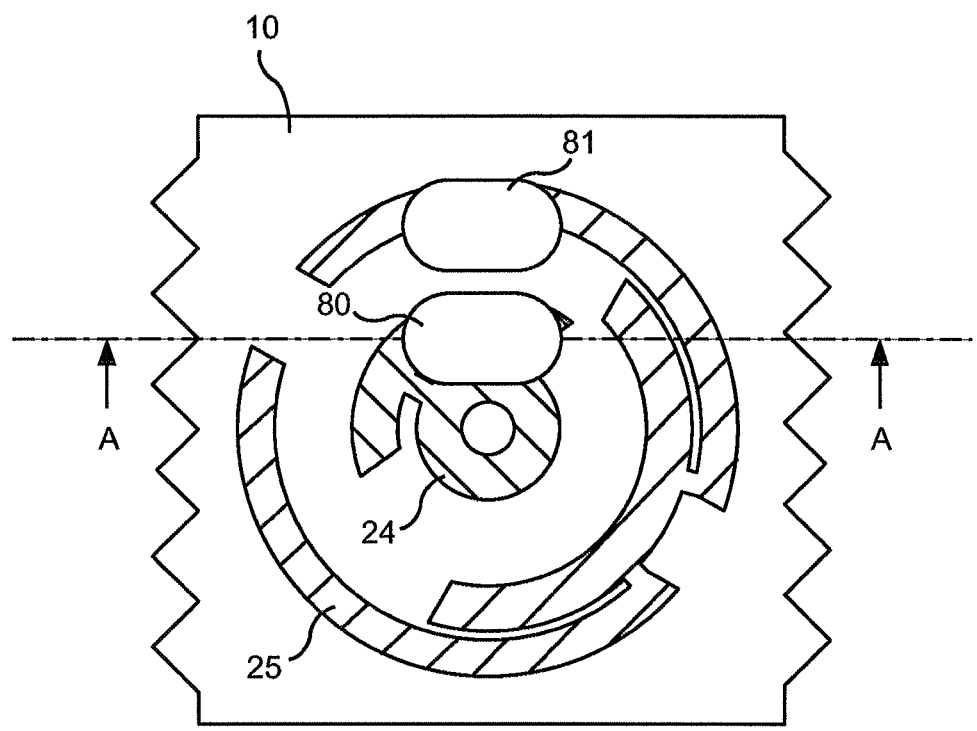
FIG. 6a shows a plan view on a pump flange having sensor component.

Possible embodiments of such an occlusion sensor are to be understood from FIGS. 6a to 12. FIGS. 6a and 6b show an embodiment in which an occlusion sensor is attached directly to the flange 10, while the occlusion sensor is integrated into a port 12, 13 in the case of the embodiments of FIGS. 7 to 12. Also both embodiments may be combined.

In the case of a proposed solution with occlusion sensor directly on the flange 10, two sensor components 80, 81 are for example applied in the form of membranes on the top side of the flange 10. In addition a respective recess 50 is provided in the flange 10, which is tightly covered with a respective sensor component. In order to be able to provide a larger surface and thereby an increased pressure sensitivity, the respective membrane is preferably distinctly wider than the width of the cavities 24, 25 accommodated on the valve plate 20.

Figure 6B:
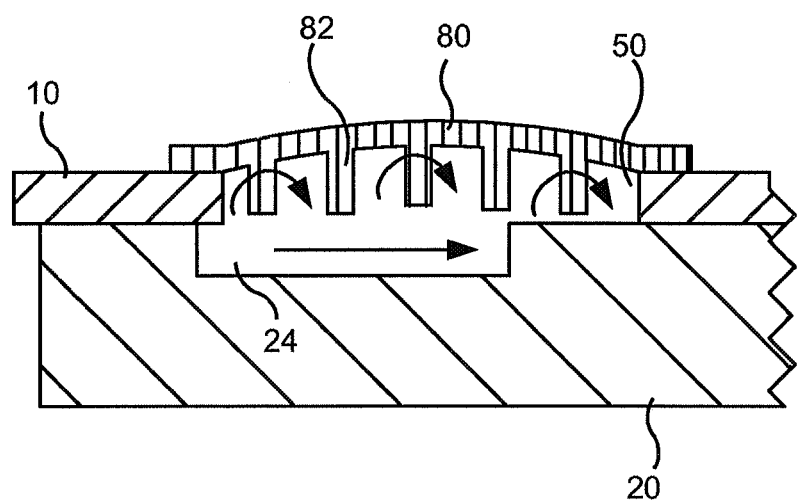

In FIG. 6b the main flow is shown with a horizontal arrow to the right. However it may possible that the volume below the membranes 80, 81 is not completely vented by this main flow. The function of the occlusion sensor is however completely provided in this case also. By means of an additional quantity of fluid which is required to compress the air, the response time is slightly delayed in the case of a not completely vented volume below the membranes 80, 81. If the membrane bottom side is provided with a simple or double spiral shaped labyrinth 82, then, upon suitable configuration of the capillary effect, an additional initial flow is induced, which can bring about a most extensive venting. This initial flow is shown in FIG. 6b by several curved arrows in the clockwise direction.

The force coming from the membranes of the sensor components 80, 81 is transferred to an external force sensor in order to recognize an occlusion. Since an occlusion in the pump feed 12 leads to a pressure vacuum upon sucking of the pump, membranes used there must already comprise a curvature by design, which curvature reduces by means of the vacuum.

An alternative embodiment of the occlusion sensor at the inlet and outlet ports 12 and 13 is shown in FIGS. 7 to 12, wherein the figures exemplarily show the relevant region in an inlet port 12 having a sensor component 40.

Figure 7:
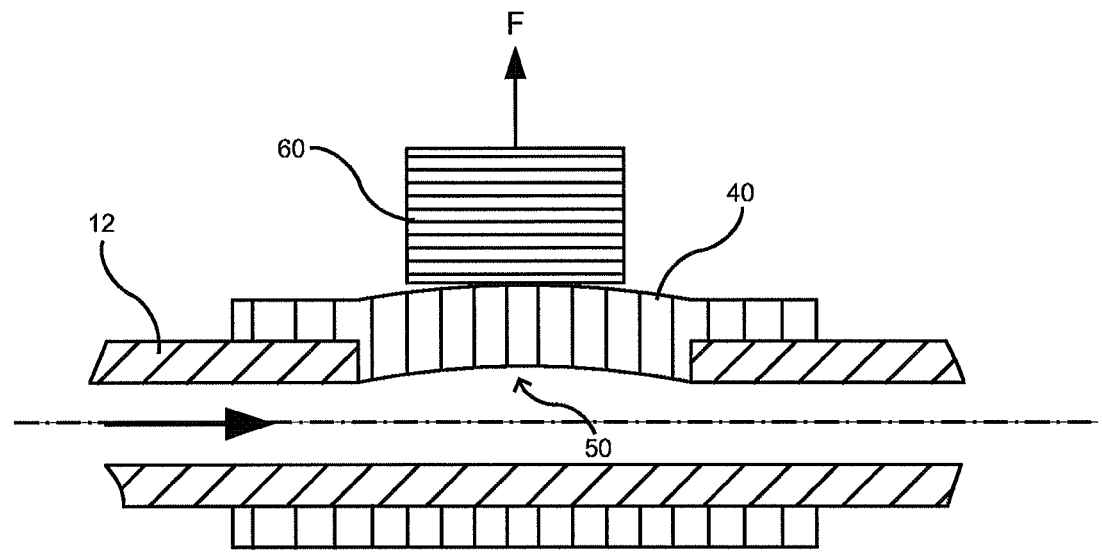
FIG. 7 shows a longitudinal section through a port having externally lying sensor component.

The longitudinal section through a port 12 shown in FIG. 7 shows an externally lying sensor component 40 which surrounds the port 12 in the region of a recess 50 with form-locking fit. A sealed connection is achieved here between the port 12 and the tubular sensor component 40. The sensor component 40 may be formed on its inner side such that it is partially inserted into the recess 50, as is shown in FIG. 7. The occlusion sensor may advantageously be made in a two-component process by injection molding, wherein the sensor component 40 is applied as a second process step after the manufacture of a tubular port 12 from a hard component. As a material for the hard component, a hard plastic may be selected, while the sensor component is composed of an elastic and pressure sensitive material such as an elastomer.

Figure 8:
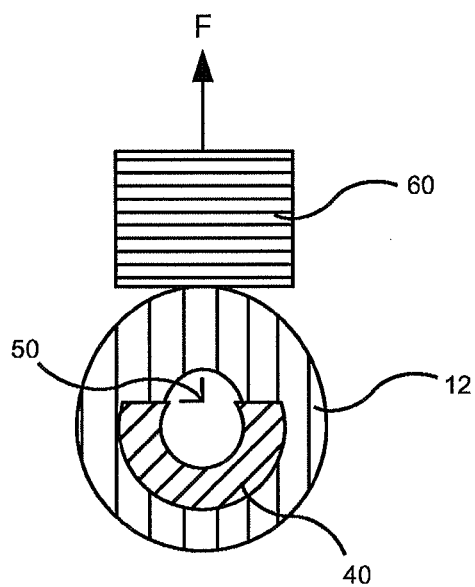
FIG. 8 shows a cross-section through a port according to FIG. 7.

The recess 50 may have an arbitrary cross-section, wherein round cross-sections have proved to be advantageous for an even force distribution. Furthermore the size of the recess 50 should be appropriately chosen. In FIG. 8 for example a cross-section through the middle of the longitudinal section of FIG. 7 is shown, whereby the recess 50 has been selected to be very deep and reaches approximately to the centerline of the port 12.

A force sensor 60 can then reach through the recess 50 so as to establish contact in this region with the outer side of the sensor component 40 and to mechanically detect the deformation of the membrane 20. This may take place for example via a plunger 60 which bears on the sensor component. When the internal pressure in the port 12 increases due to an occlusion, the sensor component 40 bends further outwardly, which can be detected by the plunger 60. When the pressure in the port 12 decreases due to an occlusion, the curvature of the sensor component 41 reduces, which also can be detected by the plunger 60.

Figure 9:
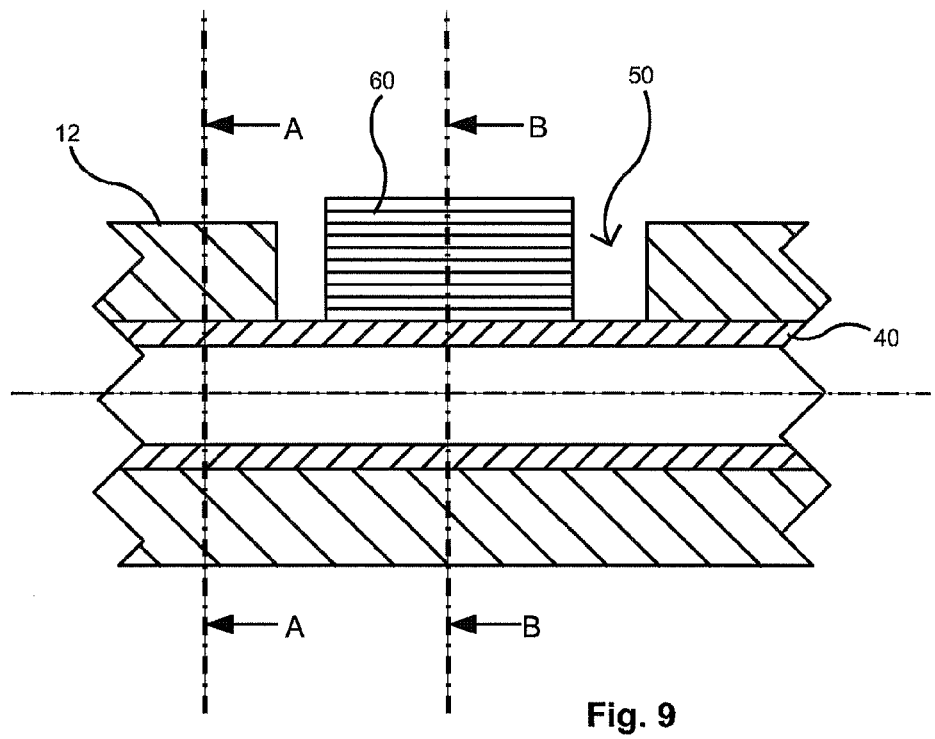
FIG. 9 shows a longitudinal section through a port having a first exemplary embodiment of an inwardly lying sensor component.

FIG. 9 shows a second exemplary embodiment of the invention, whereby a tubular sensor component 40 is attached inside a port 12 and thus tightly covers a recess 50 from inside. This occlusion sensor may equally be made in a two-component process by injection molding in the form of a continuous inner tube as soft component, while the associated inlet or outlet port is made in an integral and non-disassemblable way, as an overlying support pipe or supporting skeleton as hard component. Thereby the inner surface of the port 12 may be configured such that it keeps the tube 40 in its position and prevents an axial sliding (not shown).

Figure 10:
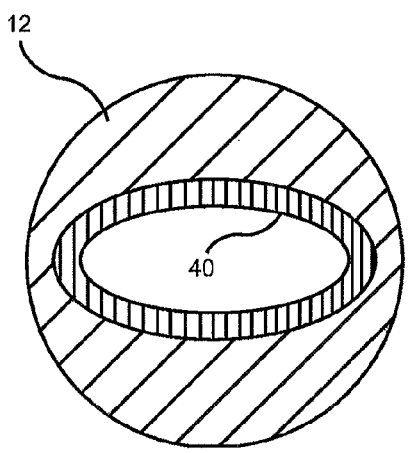
FIG. 10 shows a first cross-section through a port according to FIG. 9.
Figure 11:
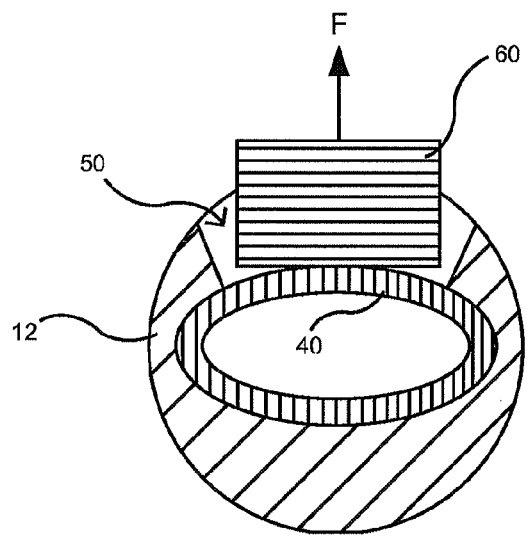
FIG. 11 shows a second cross-section through a port according to FIG. 9.

FIG. 10 Shows a first a cross-section through such a port along line A-A, whereby it can be seen that the sensor component 40 has an elliptical cross-section. The inner wall of the port 12 is suitably formed in order to be able to accommodate the sensor component 40 with form-locking fit. A second cross-section along the line B-B is depicted in FIG. 11 and shows also the plunger 60 which contacts the outer surface of the sensor component through the recess 50.

Figure 12:
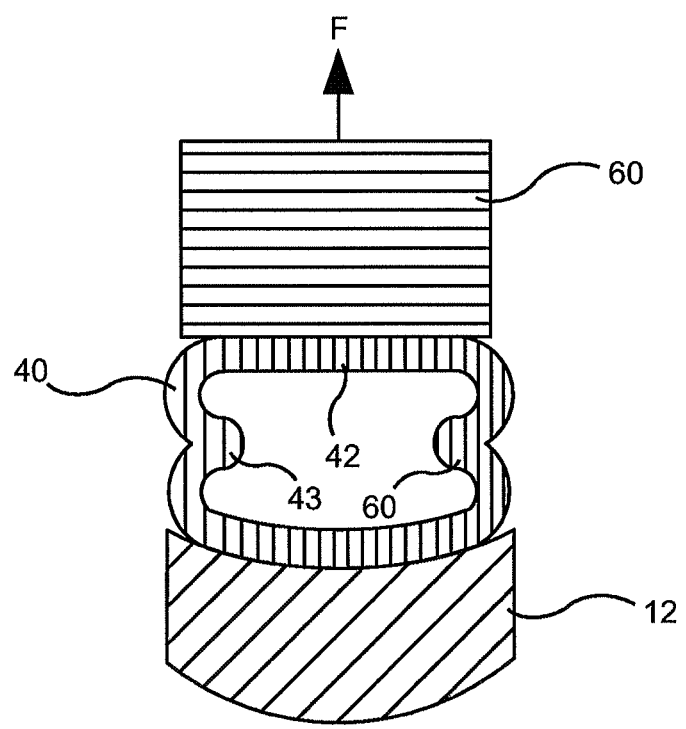
FIG. 12 shows a cross-section through a port having a second exemplary embodiment of an inwardly lying sensor component.

In order to prevent to the greatest possible extent internal stresses of the sensor component 40, this may also be configured as a specially formed measurement membrane, as is shown for example in FIG. 12. The measurement membrane 40 here comprises two opposite-lying membrane sides 43 and 44, which are kinked inwards. The membrane top side 42, which connects the two membrane sides 43, 44, is executed in a straight manner and is in contact with the plunger 60. The membrane top side 42 is no longer changed by the internal stress, which results in a linear force characteristic: force=internal pressure×membrane surface area.

The inner surface of the port 12 may then be suitably executed such that the measurement membrane 40 bears on it with form-locking fit and does not extend in undesired directions, e.g. to the side, upon a pressure rise. Also this special shape of the port 12 may be provided only in the region of the occlusion sensor, whereby costly forms within the entire port can be avoided.

The cross-section of the sensor component 40 is thus individually formed and contains at least one of the following functional components:

A straight or approximately straight line which determines the geometry of the membrane required for measurement purposes.

A straight or curved line opposite the membrane, which performs a support function of the soft component with respect to the tubular or skeletal hard component.

A geometry for the realization of a spring function on the two sides of the soft component, so that a preload can be set up, which is necessary for the measurement of pressures below ambient atmospheric pressure. In addition the spring function is necessary so that the membrane can remove itself from its opposite-lying support surface upon an increasing inner pressure.

The hard component which surrounds the plunger 60 preferably comprises a planar surface, which lies approximately underneath the plunger's upper edge. This surface serves as an abutment surface when the plunger is pushed against another surface. The plunger can then be pushed only by the amount of its overhang, whereby a constant preload for the pressure sensor is created.

In the exemplary embodiments shown in FIGS. 7 to 12, the recess 50 and thus the plunger 60 is located always at the top in the port 12, but also other arrangements may be chosen.

Figure 13:
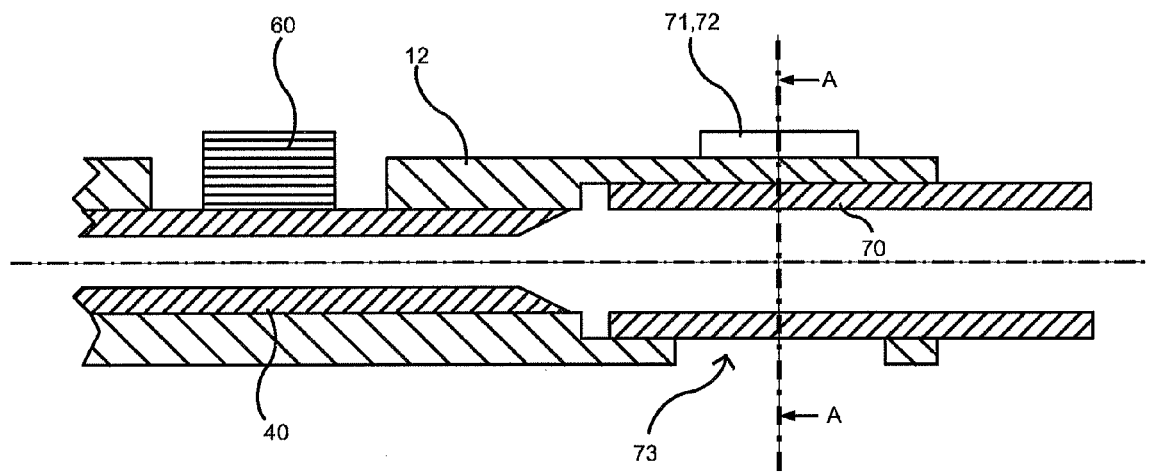
FIG. 13 shows a longitudinal section through a port with inwardly lying sensor component and ultrasound sensor.
Figure 14:
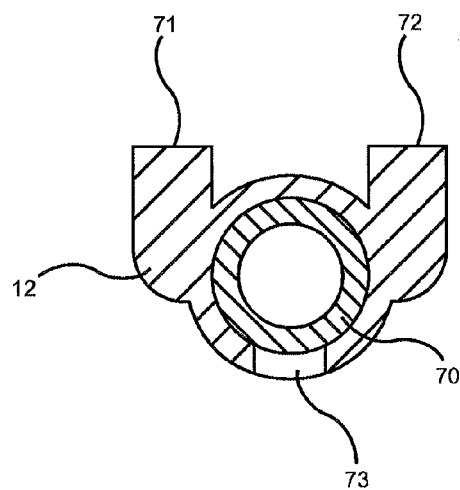
FIG. 14 shows a cross-section through a port with ultrasound sensor according to FIG. 13.

An optional ultrasound sensor for the piston pump according to aspects of the invention together with an inwardly lying sensor component 40 is shown in FIG. 13, which renders the additional manual introduction of a tube into special holders superfluous. By means of this ultrasound sensor, air bubbles in the infusion tube system can be recognized, wherein also this ultrasound sensor may be attached inside the inlet and/or outlet port 12, 13. In FIG. 13 the ultrasound sensor is shown exemplarily in the inlet port 12. For this purpose, this port 12 is suitably widened on the inside at its end such that a flexible tube 70 can be introduced there and fixed by glueing for example. The coupling and decoupling of the ultrasound occurs at two opposite-lying surfaces 71, 72 which preferably may be executed to be flat, as is shown in FIG. 14 in cross-section along line A-A. The two surfaces 71, 72 thereby lie in one plane. A recess 73 in the inlet port 12 is located opposite the flat surfaces 71, 72. However other form-locking connections, e.g. by means of a cone, are also conceivable.

As with the occlusion sensor, the mechanical components for the air bubble detection preferably also form an integral component of the tubular ports and cannot be disassembled non-destructively. Comparable adaptations of the pump apparatus for supporting the sensor are also possible, for example to allow alternative optical air bubble recognition methods or to allow the formation of defined interfaces for a measurement of temperature.

The coupling and decoupling surfaces for the ultrasound as well as the abutment surface for the occlusion sensor preferably form a plane, whereby the interface to the associated electronic sensors also forms a plane which can be located for example in a medical device. Through this means, requirements for a good and simple cleanability can be easily implemented.

The invention claimed is:

1. Piston pump for pumping a fluid, comprising:
   a central valve plate;
   at least two cylinders, each cylinder having a piston which is movable inside the associated cylinder along a longitudinal axis of the cylinder by a drive;
   a planar pump flange arranged between the central valve plate and the at least two cylinders, the planar pump flange having a first planar surface facing the at least two cylinders and a second planar surface, opposite the first planar surface, facing the central valve plate; and
   at least one inlet port and one outlet port;
   wherein the at least two cylinders are attached to the first planar surface of the planar pump flange such that the first planar surface of the planar pump flange extends along a direction of motion of the pistons, and in each cylinder a chamber is formed having a volume that changes when the associated piston is moved in the cylinder;
   wherein the at least one inlet port and one outlet port are attached to the first planar surface such that longitudinal axes of the at least one inlet port and the at least one outlet port extend along the first planar surface of the planar pump flange;
   wherein the central valve plate is attached to the second planar surface of the planar pump flange,
   wherein the central valve plate bears on the second planar surface of the planar pump flange and continuously rotates during pumping operation of the piston pump, and wherein an axis of rotation of the central valve plate runs transversely to the planar pump flange,
   wherein the planar pump flange includes at least one passage extending through the planar pump flange connecting each of the at least one inlet port and one outlet port to the central valve plate such that the planar pump flange includes at least a first passage for the inlet port and at least a second passage for the outlet port;
   wherein the planar pump flange includes at least one cylinder opening extending through the planar pump flange connecting each of the at least two cylinders to the central valve plate such that the planar pump flange includes at least a first cylinder opening for a first cylinder and at least a second cylinder opening for a second cylinder; and
   wherein the central valve plate comprises at least two cavities on a side of the central valve plate facing the second planar surface of the planar pump flange, of which a first cavity coincides, upon rotation of the valve plate to a first angular position, with the at least one first cylinder opening for the first cylinder and the at least one second passage for the outlet port, while a second cavity coincides in the first angular position with the at least one first passage for the inlet port and the at least one second cylinder opening for the second cylinder, and that the first cavity, upon rotation of the valve plate to a second angular position, coincides with the at least one second passage for the outlet port and the at least one second cylinder opening for the second cylinder, while the second cavity coincides in the second angular position with the at least one first passage for the inlet port and the at least one first cylinder opening for the first cylinder.

2. Piston pump according to claim 1, wherein upon rotation of the central valve plate to at least a third angular position, the at least two cavities of the central valve plate do not coincide with either the at least one first cylinder opening for the first cylinder or the at least one second cylinder opening for the second cylinder.

3. Piston pump according to claim 2, wherein the third angular position lies between the first and second angular positions.

4. Piston pump according to claim 1, wherein the longitudinal axes of the cylinders and/or the longitudinal axes of the at least one inlet port and one outlet port run in the same direction.

5. Piston pump according to claim 1, wherein the drive brings about the movement of the pistons as well as the rotation of the central valve plate.

6. Piston pump according to claim 1, wherein the drive is an eccentric drive having an eccentric disc and a frame surrounding the eccentric disc, wherein a rotation point (V) of the central valve plate deviates from a rotation point (E) of the eccentric disc and that a rotational drive unit brings about the rotation of the central valve plate during pumping operation of the piston pump, wherein the drive unit is coupled to the eccentric disc such that the eccentric disc rotates with the central valve plate and makes contact on the frame at two opposite-lying frame flanks, whereby the frame reciprocates in the direction of the two frame flanks, and that the pistons are each coupled to the frame such that a reciprocating motion of the frame can be transferred to the pistons.

7. Piston pump according to claim 6, wherein the eccentric disc is releasably coupled to the drive unit.

8. Piston pump according to claim 7, wherein the eccentric disc is configured to be ring-shaped, and surrounds the rotational drive unit, wherein the drive unit comprises a nose at its outer periphery while the eccentric disc comprises a pin at its inner periphery, which bears on the nose during pumping operation of the piston pump.

9. Piston pump according to claim 1, wherein at least one respective occlusion sensor is integrated into the at least one inlet port or outlet port and/or the pump flange respectively, which occlusion sensor cannot be non-destructively disassembled, wherein the inlet port, the outlet port and/or the pump flange serve as a housing of the occlusion sensor.

10. Piston pump according to claim 9, wherein in the housing at least one recess is provided which is tightly covered by a sensor component of the at least one occlusion sensor composed of a pressure sensitive material, wherein the material of the housing is harder than that of the sensor component, and that the piston pump comprises a force sensor with which pressure-induced changes of the sensor component in the region of the respective recess can be measured.

11. Piston pump according to claim 10, wherein the connection between the sensor component and a housing is an injection-molded connection made by a two-component process.

12. Piston pump according to claim 10, wherein the sensor component is tubular and is attached to an inlet and/or outlet port such that it tightly covers the respective recess from inside or from outside.

13. Piston pump according to claim 1, wherein an ultrasound sensor is integrated into an inlet port and/or outlet port respectively, for the detection of air bubbles in the respective port, which ultrasound sensor cannot be non-destructively disassembled.

14. Piston pump according to claim 13, wherein a tube is inserted into the inlet and/or outlet port with form-locking fit, through which fluid is supplied to the inlet port or discharged from the outlet port, wherein surfaces for the coupling and decoupling of ultrasound are provided in the region of the tube on two sides of the relevant inlet and/or outlet port.

15. Apparatus for supplying and metering a fluid for medical purposes, wherein the apparatus includes a piston pump according to claim 1.

* * * * *